United States Patent [19]

Hijiya et al.

[11] Patent Number: 4,831,022
[45] Date of Patent: May 16, 1989

[54] INCLUSION COMPOUND OF EICOSAPENTAENOIC ACID AND FOOD PRODUCT CONTAINING THE SAME

[75] Inventors: Hiromi Hijiya; Masakazu Mitsuhashi; Toshi Miyake, all of Okayama, Japan

[73] Assignee: Kabushiki Kaisha Hayashibara Seibutsu Kagaku Kenkyujo, Okayama, Japan

[21] Appl. No.: 244,808

[22] Filed: Sep. 15, 1988

Related U.S. Application Data

[62] Division of Ser. No. 843,645, Mar. 25, 1986, Pat. No. 4,777,162, which is a division of Ser. No. 636,901, Jul. 31, 1984, Pat. No. 4,775,749.

[30] Foreign Application Priority Data

Aug. 8, 1983 [JP] Japan .................... 58-144693

[51] Int. Cl.$^4$ ............. C08B 37/16; A61K 31/19; A61K 31/715
[52] U.S. Cl. ................. 514/58; 424/439; 424/440; 424/441; 426/658; 536/103

[58] Field of Search ............ 514/58; 426/658; 536/103; 424/439, 440, 441

[56] References Cited

U.S. PATENT DOCUMENTS

| 4,380,626 | 4/1983 | Szejtli et al. | 536/103 |
| 4,438,106 | 3/1984 | Wagu et al. | 536/103 |
| 4,524,068 | 6/1985 | Szejtli et al. | 536/103 |

FOREIGN PATENT DOCUMENTS 2104907A  3/1983  United Kingdom ........ 536/103

Primary Examiner—Ronald Griffin
Attorney, Agent, or Firm—Browdy & Neimark

[57] ABSTRACT

A novel EPA/CD inclusion compound and a food product containing the same are disclosed. The undesirable odor of EPA is masked by including it into such EPA/CD inclusion compound. Gamma-CD is most favorable because it includes much more EPA, and highly stabilizes it. The EPA/CD inclusion compound is advantageously usable in perorally- or parenterally-usable products directed to the promotion or maintenance of health.

16 Claims, 2 Drawing Sheets

INCLUSION COMPOUND OF EICOSAPENTAENOIC ACID AND FOOD PRODUCT CONTAINING THE SAME

This is a division of application Ser. No. 843,645, filed Mar. 28, 1986, now U.S. Pat. No. 4,777,162 issued Oct. 11,1988, itself a division of earlier application Ser. No. 636,901, filed July 31,1984 now U.S. Pat. No. 4,775,749, issued Oct. 4,1988.

FIELD OF THE INVENTION

The present invention relates to a cyclodextrin inclusion compound of eicosapentaenoic acid, and to a food product containing the compound. More particularly, it relates to a gamma-cyclodextrin inclusion compound containing about 20°-50 w/w % eicosapentaenoic acid, and to a food product containing the same.

Eicosapentaenoic acid, cyclodextrin, and inclusion compound thereof will be abbreviated hereinafter as "EPA", "CD" and "EPA/CD" respectively.

BACKGROUND OF THE INVENTION

As is evident from *Up-to-Date Foodprocessing*, Vol.17, No.11, pp.15–22 (1982), it is known that EPA prevents arteriosclerosis, inhibits the aggregation of blood platelets, and decreases the levels of serum cholesterol and neutral fats. In recent years, EPA has been commercialized as a thrombolytic agent to prevent cardiac- or brain infarction, as well as an agent to promote and maintain health.

It has been confirmed that administration of EPA should be continued for a long period, for example, along with a food product because unlike pharmaceuticals such as antibiotics a dramatic restoration or recovery can not be expected with one to several dosages of EPA.

Also was confirmed that EPA is difficult to ingest because it is an oily substance having a characteristic odor of fresh blue skinned fishes such as sardine or mackerel, as well as that it is very unstable due to its high susceptibility to rancidification. These facts render an EPA administration over long period even with a small dose very difficult.

In Japan Patent Kokai No.13,541/83 (WAGU, Masakatsu et al.), an EPA/CD inclusion compound produced with a water-methanol system is disclosed. It is apparent that the inclusion compound obtained in this way, however, is very low in EPA content, i.e. only 4–15 w/w %.

DETAILED DESCRIPTION OF THE INVENTION

Figure 1:
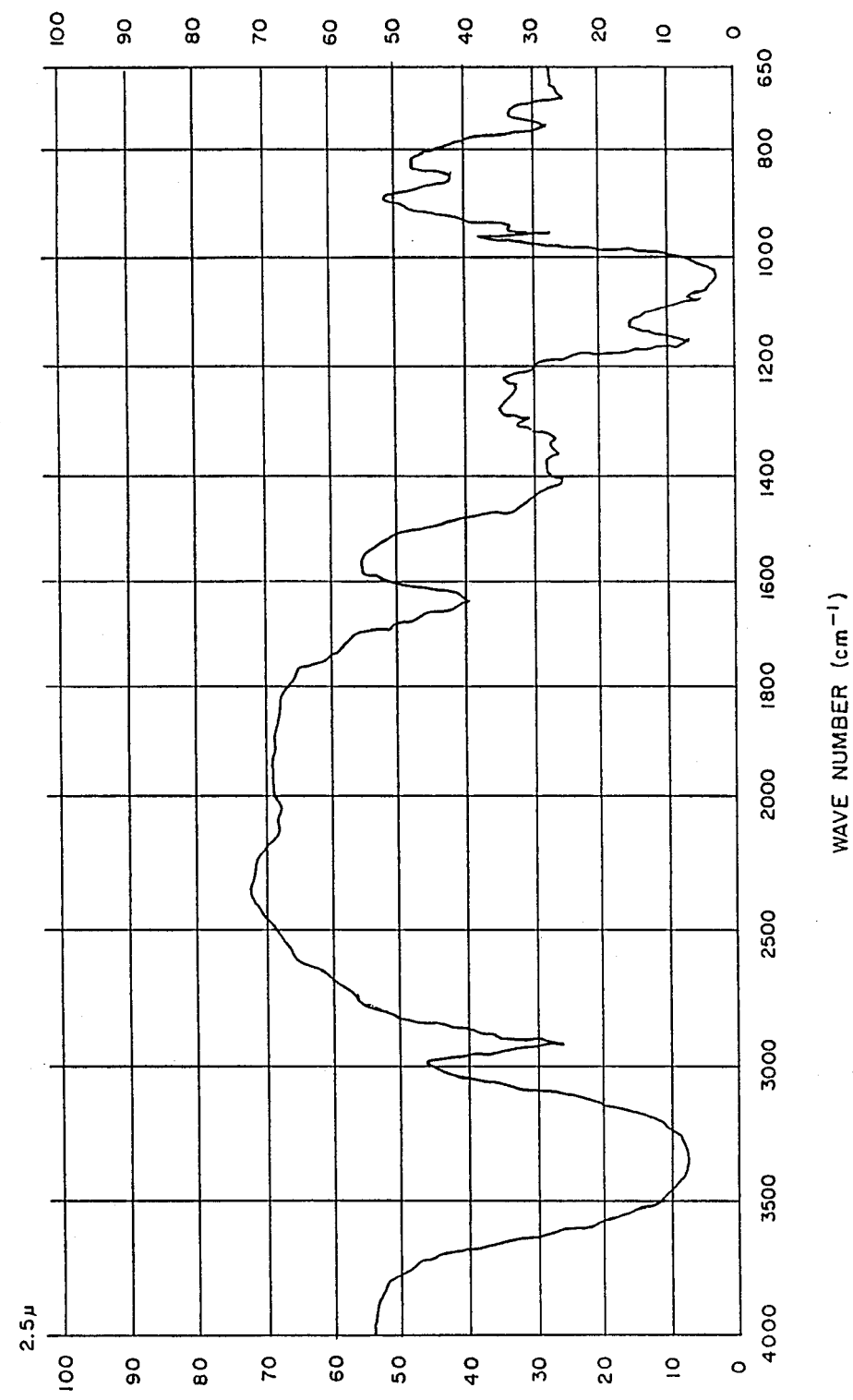
FIGs.1 and 2 show the infrared spectra of the EPA/alpha-CD and EPA/gamma-CD inclusion compounds respectively.

Accordingly, in order to expand the utilization of EPA to food products directed to a prolonged use, the present inventors diligently investigated various means whereby the undesirable odor and susceptibility to rancidification of EPA can be masked or suppressed, and whereby EPA is water-solubilized and imparted with an emulsifying property, while retaining the inherent physiological activities of EPA. As a result, we found eventually a novel EPA/CD inclusion compound having an EPA content much higher than that in conventional EPA/CD inclusion compound, i.e. EPA content of about 20°-50 w/w %, which can be obtained by including EPA under hydrous conditions to form an EPA/gamma-CD inclusion compound. Thus, the present inventors accomplished the present invention.

The EPA as referred to in the invention shall not be restricted to a high-purity EPA, and includes EPA per se and also its derivatives such as salts and esters, in addition to crude preparations which additionally contain other highly-unsaturated fatty acid such as docasahexaenoic acid or its derivative.

The CDs usuable in the invention are gamma-CD which is obtainable from starch or amylose with the aid of cyclodextrin glucanotransferase (EC 2.4.1.19), and also saccharified starch products containing the same. In comparison with other CDs, e.g. alpha- or beta-CD, gamma-CD includes much more EPA and much more stabilizes it. Furthermore, gamma-CD per se is highly susceptible to alpha-amylase when perorally or parenterally administrated. These features of gamma-CD are advantageous in the incorporation of EPA.

As to the procedures to prepare the EPA/gamma-CD inclusion compound, the saturation solution method and kneading method are feasible. Particularly, the latter method containing the step of kneading EPA and gamma-CD under hydrous conditions is favorable. It was confirmed that a satisfiable inclusion compound can be obtained by the kneading method by use of relatively small amounts of water and EPA, i.e., equivalent or less against the amount of gamma-CD. Also, it was confirmed that the EPA/gamma-CD inclusion compound so obtained retains the inherent physiological activities of EPA, but, unlike intact EPA, is almost freed of undesirable odors, and that the inclusion compound is much less susceptible to deterioration or rancidification.

The EPA/gamma-CD inclusion compound may be ingested intact, or, if necessary, dried, pulverized and prepared into desirable shape, e.g. granule or tablet, prior to its use. Furthermore, the inclusion compound may be supplemented with an appropriate amount of mineral, vitamin or crude drug. Also, they may be colored, flavored, or seasoned in a suitable manner, prior to its use.

The wording of "food product(s)" as referred to in the invention means all perorally- or parenterally-usable products capable of transporting an effective amount of the EPA/gamma-CD inclusion compound into the body to promote or maintain health. The perorally-usable products include, for example, seasonings, confectioneries, meat products, including fish meat products, dairy products beverages, and drugs for internal uses; and the parenterally-usuable products include, for example a liquid food for oral administration, hyperalimentation, and cosmetics.

The present invention will be further explained with reference to the following Experiment.

EXPERIMENT

Preparation of EPA/CD inclusion compounds

Several EPA/CD inclusion compounds were prepared.

To 20 g aliquots of alpha-, beta- or gamma-CD were added 15 ml aliquots of water and a commercial high-purity EPA in respective amount of 2, 5, 10, 20, 30 or 40 g, and the mixtures were kneaded for 10 minutes. After drying by heating at 100° C. for 2 hours, the resultant was washed with chloroform, and dried to obtain EPA/CD inclusion compounds.

The EPA contents in the inclusion compounds were determined as follows: 100 mg of the inclusion compound was added with 10 ml of a mixture solution of chloroform and methanol (2:1), and shaken for 1.5 hours to effect extraction. The supernatant of the resultant was then determined on absorbance at a wavelength of 244 nm. The results are given in Table 1.

As is evident from the results given in Table 1, an EPA/CD inclusion compound is formed, regardless of the CD used. It was confirmed that the EPA content in the inclusion compounds is in the range of about 1-50 w/w %, but very variable dependent on the types of the CD used: when alpha-CD is used, the EPA content is up to 10 w/w %; beta-CD, up to 5 w/w %; and gamma-CD, up to 50 w/w % is 10-fold higher than that attained with beta-CD. Each inclusion compound gave an emulsion when dissolved in water to give respective concentration of 0.5 w/w %.

The product obtained by kneading EPA together with alpha-, beta- or gamma-CD but without use of water is not an inclusion compound, but a mere mistake. In such mixture of CD and EPA, the undesirable odor was not masked, and the EPA oil floated on water when added with water to give a concentration of 0.5 w/v %.

TABLE 1

| Test No. | Amount used CD (g) | EPA (g) | EPA content in inclusion compound as solid (w/w %) |
|---|---|---|---|
| 1 | alpha-CD 20 | 5 | 4.6 |
| 2 | alpha-CD 20 | 10 | 8.3 |
| 3 | alpha-CD 20 | 20 | 10.1 |
| 4 | alpha-CD 20 | 30 | 10.4 |
| 5 | alpha-CD 20 | 40 | 9.8 |
| 6 | beta-CD 20 | 5 | 1.9 |
| 7 | beta-CD 20 | 10 | 2.8 |
| 8 | beta-CD 20 | 20 | 4.3 |
| 9 | beta-CD 20 | 30 | 4.6 |
| 10 | beta-CD 20 | 40 | 4.8 |
| 11 | gamma-CD 20 | 5 | 5.2 |
| 12 | gamma-CD 20 | 10 | 19.5 |
| 13 | gamma-CD 20 | 20 | 42.3 |
| 14 | gamma-CD 20 | 30 | 43.1 |
| 15 | gamma-CD 20 | 40 | 47.6 |

Since the EPA/gamma-CD inclusion compound according to the invention is emulsifiable, it is advantageously usable in a variety of food products such as those in oil-, water- or emulsion-phase.

The properties of EPA/CD inclusion compounds Nos.3 and 13 listed in Table 1 were investigated.

The pH level in 0.2 w/v % aqueous solutions of these inclusion compounds were 5.1 and 4.1 respectively. Their uv-spectra in aqueous solution showed no characteristic adsorption when analyzed by uv-spectrometry.

Figure 2:
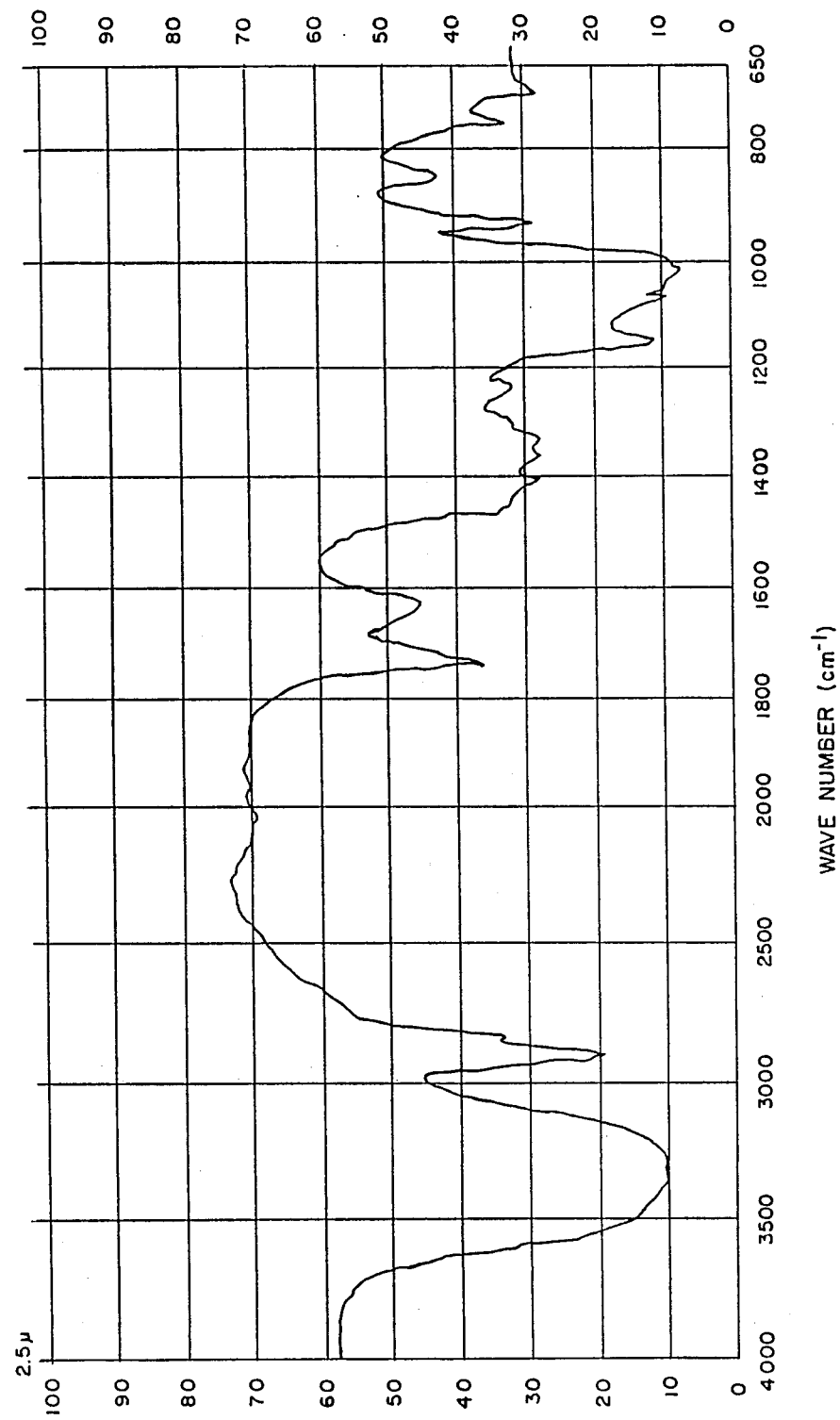

The infrared spectra of the EPA/alpha-CD and EPA-gamma-CD inclusion compounds were determined by the KBr-tablet method, and are given in FIGS.1 and 2 respectively.

The invention will be understood more readily with reference to the following examples.

EXAMPLE 1

Powder containing EPA/gamma-CD inclusion compound

Forty g of gamma-CD was added with 40 ml of water and 30 g of a commercial high-purity EPA, and the mixture was kneaded for 15 minutes, dried in vacuo at 60° C. for 4 hours, and pulverized to obtain about 70 g of the captioned product.

This inclusion compound was a pale yellow powder almost freed of undesirable odor. Furthermore, this inclusion compound was very stable because of its lower susceptibility to rancidification.

EXAMPLE 2

Powder containing EPA/gamma-CD inclusion compound

One hundred g of gamma-CD was added with 70 ml of water and 140 g of a commercial crude EPA, EPA content of about 50 w/w %, and the mixture was kneaded for 15 minutes and dried at 90° C. for 2 hours. The resultant dry solid was washed with chloroform, and dried at 100° C. for an additional 2 hours to obtain about 180 g of a crude EPA/gamma-CD inclusion compound.

This inclusion compound was a pale yellow powder having an EPA content of about 30 w/w % and almost freed of undesirable odor. Furthermore, this inclusion compound was very stable because of its lower susceptibility to rancidification.

EXAMPLE 3

Syrup containing EPA/gamma-CD inclusion compound

Five kg of a commercial starch syrup containing 200 g gamma-CD, moisture content of about 20 w/w %, was added with 150 g of a commercial high-purity EPA, and the mixture was vigorously stirred under nitrogen atmosphere for 30 minutes while cooling to 10° C. to obtain the captioned product.

This inclusion compound was a white milky syrup almost freed of undesirable odor, and the EPA component was less susceptible to rancidification.

EXAMPLE 4

Hard Candy

Six kg of sucrose, 3 kg of "SUNMALT ®", a crystalline maltose powder commercialized by Hayashibara Co., Ltd., Okayama, Japan, and 1 kg of a syrup containing EPA/gamma-CD inclusion compound, prepared by the method as described in Example 3, where dissolved in 5 liters of water while heating, and the solution was boiled up to 145°-150° C., concentrated in vacuo to give a moisture content of below 2 w/w %, added with 80 g of citric acid and small amounts of lemon flavor and coloring agent, and sharped in usual way to obtain the captioned product.

The product is a suitable hard candy exhibiting the inherent physiological activities of EPA, e.g. arteriosclerosis-preventing activity.

EXAMPLE 5

Chocolate

Forth kg of cacao paste, 10 kg of cacao butter, 15 kg of powdered sugar, 15 kg of whole milk and 500 g of a powder containing EPA/gamma-CD inclusion compound, prepared by the method as described in Example 1, were admixed, and passed through a refiner to reduce its particle size. The content was then placed in a conche, added with 500 g of lecithin, and kneaded therein at 50° C. for 2 days. The content was placed in a mold, and solidified therein to obtain the captioned product.

The product is excellent in texture and flavor, and free from fator sugar-blooming during storage. The product is a suitable chocoolate exhibiting the inherent physiological activities of EPA, e.g. anticholesteremic and serum neutral fats-decreasing activities.

EXAMPLE 6

Carbonated beverage

In 8 liters of water was dissolved 1.97 kg of a commercial isomerized sugar solution (conversion degree 55%), 15 g of a powder containing EPA/gamma-CD inclusion compound, prepared by the method as described in Example 2, 23 g of citrix acid, 0.2 g of vitamin $B_1$ nitrate and 0.5 g of vitamin $B_6$ while stirring, and the resultant solution was gassed in conventional manner with 2 volumes of carbon dioxide with the aid of a carbonator to obtain the captioned product.

The product is a suitable health-promoting beverage exhibiting the inherent physiological activites of EPA.

EXAMPLE 7

Jelly

One and half kg of sucrose, 30 g of sodium citrate, 110 g of "GF-100", a stabilizer commercialized by Nitta Gelatine Co., Ltd., Osaka, Japan, 10 g of an EPA/gamma-CD inclusion compound, prepared by the method as described in Test No. 13 in Experiment 1, and 7.3 liters of water were mixed while heating. The mixture was kept at 80° C. for 10 minutes, and admixed with 1 kg of prune extract (moisture content 30 w/w %) and 30 g citrix acid in a minimum amount of water while stirring. The resultant was packed in a vessel at 60°–70° C., sterilized at 90° C. for 30 minutes, and cooled to obtain the captioned product.

The product is a jelly having a refreshing taste and sweetness. The product is a suitable health-promoting jelly exhibiting the inherent physiological activities of EPA.

EXAMPLE 8

Tablet

One hundred g of "SUNMALT®", a crystalline maltose powder commercialized by Hayashibara Co., Ltd., Okayama, Japan, 10 g of corn starch, and 10 g of a powder containing an EPA/gamma-CD inclusion compound, prepared by the method as described in Example 1, were admixed, and the mixture was shaped by use of a tabletting machine, equipped with 20 R-punch of 12 mm diameter, into tablet of 680 mg each having a thickness of 5.25 mm and a hardness of 8±1 kg.

The product is an easily administrable tablet having the inherent physiological activities of EPA, e.g. arteriosclerosis preventing activity, blood platelet aggregation inhibiting activity, anticholesteremic activity, and serum neuatral fats decreasing activity.

EXAMPLE 9

Emulsion

Nine kg of soybean oil, 1 kg of a powder containing EPA/gamma-CD inclusion compound, prepared by the method as described in Example 1, 1 kg of egg lecithin, 10 kg of maltose and 90 liters of water were admixed with a mixer in usual way to obtain a partially-emulsified liquid. The liquid was then further emulsified with a high pressure mixer to obtain an oil-inwater emulsion having an average particle size of 0.01–0.3μ. The emulsion was treated with a membrane filter to remove bacteria, distributed into vial, capped, and sterilized by heating to obtain an emulsion for hyperalimentation.

The product exhibiting the inherent physiological activities of EPA is a suitable emulsion for hyperalimentation and peroral- or parenteral intubation feeding, as well as for high-caloric supplement.

While specific details have been shown and described, it would be understood that changes and alterations may be resorted to without departing from the spirit of the invention as defined in the appended claims.

We claim:

1. A composition, comprising gamma-cyclodextrin (gamma-CD) and eicosapentaenoic acid (EPA) of an amount in the range of 20–50 w/w % against gamma-CD, wherein the EPA molecules are included in the cyclic gamma-CD molecules, which is a cosmetic.

2. A process for producing a gamma-CD inclusion compound of EPA, said process containing the step of:
    admixing gamma-CD and EPA to homogeneity under hydrous conditions.

3. A process as set forth in claim 2, said process comprises:
    admixing gamma-CD and EPA to homogeneity under hydrous conditions; and
    drying the resultant mixture.

4. A process as set forth in claim 2, said process comprises:
    admixing gamma-CD and EPA to homogeneity under hydrous conditions;
    drying the resultant mixture;
    treating the solid with chloroform; and
    drying the solid.

5. A process as set forth in claim 2, said process comprises:
    admixing gamma-CD and EPA to homogeneity under hydrous conditions; and
    treating the resultant mixture under nitrogen atmosphere.

6. A gamma-CD inclusion compound of EPA whenever prepared by the process as claimed in claim 2.

7. A process for producing a food product, said process containing the step of:
    incorporating an effective amount of a gamma-CD inclusion compound of EPA with a food product.

8. A process as set forth in claim 7, wherein said food product is perorally used.

9. A process as set forth in claim 7, wherein said food product is parenterally used.

10. A process as set forth in claim 7, wherein said food product is an emulsion.

11. A process as set forth in claim 7, wherein said food product is a health food or a health beverage.

12. A process as set forth in claim 7, wherein said food product is a fluid food.

13. A process as set forth in claim 7, wherein said food product is a hyperalimentation.

14. A process as set forth in claim 7, wherein said inclusion compound is obtained by the process containing the step of:
    admixing gamma-CD and EPA to homogeneity under hydrous conditions.

15. A process as set forth in claim 7, wherein the EPA content in said inclusion compound is in the range of 20–50 w/w %.

16. A food product whenever produced by the process as claimed in claim 7.

* * * * *